United States Patent [19]

Brill

[11] 4,115,421

[45] Sep. 19, 1978

[54] PROCESS FOR CONVERTING THALLIUM (I) TO THALLIUM (III)

[75] Inventor: William F. Brill, Skillman, N.J.

[73] Assignee: Halcon International, Inc., New York, N.Y.

[21] Appl. No.: 740,144

[22] Filed: Nov. 8, 1976

Related U.S. Application Data

[63] Continuation-in-part of Ser. No. 691,114, May 28, 1976, abandoned.

[51] Int. Cl.$^2$ ............................................. C07F 5/00
[52] U.S. Cl. ................................... 260/429 R; 423/395; 423/495; 423/544; 423/659
[58] Field of Search ..................... 260/429 R; 423/395, 423/495, 544

[56] References Cited

U.S. PATENT DOCUMENTS

| | | | |
|---|---|---|---|
| 3,399,956 | 9/1968 | Hirose et al. | 423/495 |
| 3,436,409 | 4/1969 | Hill et al. | 260/348.5 |
| 3,479,262 | 11/1969 | MacLean et al. | 204/80 |
| 3,792,069 | 2/1974 | Baird et al. | 423/544 |
| 3,816,540 | 6/1974 | Barone et al. | 260/610 B |

OTHER PUBLICATIONS

Spencer, L., Anorg. Chem., vol. 44, pp. 379–399 (1905).
Spencer, L., Anorg. Chem., vol. 44, pp. 399–407 (1905).
Spiro et al., J. Chem. Soc., pp. 78 to 96 (1965).
Chemical Abstracts, 64, 13800h (1966).
Chemical Abstracts, 67, 96732e (1967).
Chemical Abstracts, 63, 1471a (1965).
Chemical Abstracts, 73, 47165e (1970).

*Primary Examiner*—Helen M. S. Sneed
*Attorney, Agent, or Firm*—William C. Long; David Dick; Jack B. Murray, Jr.

[57] ABSTRACT

A mcnovalent thallium compound is converted to a trivalent thallium compound by treating the thallium (I) compound with an organic hydroperoxide in the presence of a Group VIII noble metal catalyst in a liquid medium to oxidize the thallium (I) compound to a thallium (III) compound.

6 Claims, No Drawings

PROCESS FOR CONVERTING THALLIUM (I) TO THALLIUM (III)

RELATED APPLICATION

This is a continuation-in-part of application Ser. No. 691,114, filed May 28, 1976 now abandoned.

This invention relates to the oxidation of thallium (I) to thallium (III).

Trivalent thallium compounds, i.e., thallic compounds, have been used as oxidizing agents in various reactions. For example, Kruse et al, J. Org. Chem. 36, 1154 (1971) describes the epoxidation of certain olefins with thallic acetate and in co-pending application Ser. No. 679,584, filed Apr. 23, 1976, now U.S. Pat. No. 4,021,453 it is disclosed that thallic aryl carboxylates are surprisingly effective as epoxidation agents.

In all of these reactions the trivalent thallium is reduced to the monovalent state and if the thallium is to be reused in the reaction it is necessary to reoxidize or "regenerate" it by converting thallium (I) to thallium (III). Various methods for effecting this conversion have been proposed and are more or less effective. Thus, Hirose et al. U.S. Pat. No. 3,399,956 describes the oxidation of Tl(I) to Tl(III) by means of molecular oxygen in an acidic aqueous medium containing a chloride or bromide ion and an ion of a redox metal such as copper, mercury, chromium, manganese, iron, cobalt and nickel. Hirose et al refer to earlier processes for effecting the conversion of Tl(I) to Tl(III) and point out the problems involved in achieving the desired oxidation and the disadvantages and drawbacks of prior procedures. While the Hirose et al process is described as an improvement over processes previously proposed, it is limited to the use of aqueous chloride or bromide solutions so that the thallium (III) is always produced as a chloride or bromide and it is generally necessary to use the redox metal in large amounts in relation to the thallium compound being treated.

It is, accordingly, an object of the present invention to provide an improved process for the oxidation of monovalent thallium to trivalent thallium.

It is a further object of the invention to provide a process of the character indicated which is not limited to specific reaction media.

In accordance with the invention, a monovalent thallium compound is converted to a trivalent thallium compound by treating the thallium (I) compound with an organic hydroperoxide in the presence of a Group VIII noble metal catalyst in a liquid medium to oxidize the thallium (I) compound to a thallium (III) compound in a rapid and efficient manner.

The Group VIII noble metals comprise platinum, palladium, rhodium, ruthenium, osmium and iridium, all of which may be used as catalysts in the process of this invention but platinum, palladium, ruthenium and rhodium are preferred, especially platinum and ruthenium. Mixed catalysts can be used if desired. The catalyst is preferably used in a heterogenous system, i.e., in the form of a suspension in the reaction medium and in this case the catalyst is ordinarily supported upon a solid carrier, but it is also possible to use the catalyst in a homogenous system, i.e., it may be employed in a form which is soluble in the reaction medium. Thus, the Group VIII noble metal catalyst may be suitably added as a compound of the above-mentioned metals, preferably on a carrier, but it is possible to add the catalyst as the finely-divided metal, e.g., platinum black, or as the metal supported on a carrier. In the case of a homogenous system, the metal is eventually converted to a compoud sufficiently soluble to provide a catalytic amount of the metal in solution in the reaction mixture. The nature of the compound of the Group VIII noble metal is not critical and any convenient compound may be used. For example, typical compounds include the oxides, the inorganic salts such as the salts of mineral acids, e.g., the chlorides and oxychlorides, the iodides, the fluorides, the phosphates, the sulfates and the sulfites, the sulfides, and the hydroxides. Other typical compounds include salts of organic acids such as acetates or other carboxylates, organo-metallic compounds such as tetramethyl platinum, carbonyls and carbonyl halides. Also various chelates, association compounds and enol salts may be used. Further illustrative of such compounds are palladium acetate, rhodium chloride, platinum oxide (Adams catalyst), chloroplatinic acid, platinum tetrachloride, platinum diamino dinitrite platinum cyanide, sodium tetrachloro platinite, potassium tetrachlo platinate, platinum dicarbonyl dichloride, platinum acetyl acetonacetate, tetrakis (triphenyl phosphine) platinum, tetramine platinum chloride, and corresponding compounds of the other Group VIII noble metals.

When the Group VIII noble metal catalyst is supported upon a carrier, the carrier or substrate which is employed is suitably in the form of a porous solid of such size that it can be readily dispersed in the liquid reaction medium, e.g., from 400 mesh/inch to ½ inch particle size. Such carrier materials are exemplified by pumice, alumina, silica, silica-alumina, magnesia, diatomaceous earth, bauxite, titania, zirconia, clays, both natural and acid treated such as Super-Filtrols, attapulgus clay (attapulgite), lime, magnesium silicate, silicon carbide, activated and unactivated carbons, zeolites as well as the zeolitic molecular sieves, solid foams, such as ceramic honeycombs, and porous organic polymers. The above carriers are suitably used in the form of regular and irregular particles such as tubes, balls, broken pieces, and the like. Such supported forms of the Group VIII noble metals and their compounds are prepared by conventional methods, e.g., deposition from a solution, for example as described in Schultz U.S. Pat. No. 3,717,670 in connection with rhodium compounds and, indeed, many such supported catalysts are available commercially, particularly in the case of the zero valent free metal.

Concentrations of the Group VIII noble metal component on the support can vary widely but illustrative concentrations lie within the range of 0.1 to 20 wt. %. Higher concentrations may, however, be used if desired.

The ratio of catalyst to monovalent thallium compound used in the process of the invention can also vary over a wide range. For example 0.1 to 40 mols of catalyst per 100 mols of monovalent thallium compound are advantageously used, but lesser or greater amounts may be employed if desired, the upper limit being determined only by economic considerations and the lower limit only by the amount which will be catalytically effective. In any case, it is a feature of the invention that only catalytic quantities are required to bring about a rapid conversion.

The reaction of this invention is carried out broadly using an organic hydroperoxide reactant having the formula ROOH wherein R is an organic radical. In preferred practice R is a substituted or unsubstituted alkyl, cycloalkyl, aralkyl, aralkenyl, hydroxyaralkyl, cycloalkenyl, hydroxycycloalkyl, and the like radical having about 3 to 20 carbon atoms. R may be a heterocyclic radical, preferably 4 to 10 and most preferably 5 to 8 carbon atoms. Illustrative hydroperoxides are cumene hydroperoxide, ethylbenzene hydroperoxide, tertiary butyl hydroperoxide, tetralin hydroperoxide, methylcyclohexene hydroperoxide, and the like as well as the hydroperoxides of toluene, p-ethyl toluene, isobutylbenzene, diisopropyl benzene, p-isopropyl toluene, o-xylene, m-xylene, p-xylene, phenyl cyclohexane, etc. Particularly preferred are tertiary butyl hydroperoxide and ethylbenzene hydroperoxide. Hydroperoxides are well-known compounds which are readily produced in known manner by the oxidation of the corresponding hydrocarbon as described, for example, in Barone et al U.S. Pat. No. 3,816,540, to which reference is made to examples of other hydroperoxides which are suitably used in the process of this invention.

The ratio of organic hydroperoxide to thallium compound can vary over a wide range but suitably at least 0.1 mol of hydroperoxide per mol of thallous compound is used. There is no particular advantage in using more than one mol of hydroperoxide per mol of thallium compound but greater quantities can, of course, be used, e.g., up to 10 mols per mol. All of the hydroperoxide can be initially charged or it can be added in portions as the reaction proceeds, e.g., dropwise.

An advantage of this invention is the fact that during the oxidation reaction the organic hydroperoxide, ROOH, is converted to the corresponding alcohol, ROH. This alcohol can itself be recovered as a valuable coproduct of the process or reconverted to the hydroperoxide by procedures such as dehydration to olefin, hydrogenation of the olefin, and oxidation to hydroperoxide, or by hydrongenolysis to hydrocarbon followed by oxidation to hydroperoxide. Thus the oxidizing agent is, during the oxidation, converted to a product suitable for convenient regeneration of the hydroperoxide for further use.

Ordinarily, the higher the reaction temperature, the greater the reaction rate. It is unnecessary, however, to employ high temperatures. Normally, the reaction temperature may range from room temperature to about 150° C. Typically, temperatures of 20° C. to 100° C. are used, but higher or lower temperatures are operable but excessively high temperatures are not advantageous because they may eventually result in reaction between the thallium compounds and the solvent.

Pressure is not a parameter of the process and subatmospheric, atmospheric or superatmospheric pressures can be used. Ordinarily, atmospheric pressure is entirely suitable. It is generally desirable to stir the reaction medium particularly when a heterogenous catalyst is employed, and this may be effected by mechanical agitation, shaking, and like means known to the art.

Any convenient monovalent thallium compound can be treated in accordance with the invention. Typically, the compound will be a salt which may be organic, such as a carboxylate of an alkyl, cycloalkyl or aryl carboxylic acid containing up to 20 carbon atoms, such as an acetate or benzoate, or inorganic, such as a nitrate, a sulfate, or a halide, but other compounds may be used, if desired. The thallous compound is suitably one which is at least partly soluble in the liquid medium used.

The thallous compounds resulting from the epoxidation reactions described in the above-mentioned Kruse et al article and in co-pending application Ser. No. 679,584, now U.S. Pat. No. 4,021,453 will be carboxylates and it is a feature of this invention that such thallous carboxylates can be converted to the thallic carboxylates with ease so that the conversion products can be directly recycled to the epoxidation reaction.

The reaction medium for the conversion of monovalent thallium to trivalent thallium can be aqueous or non-aqueous. Non-aqueous media comprise organic solvents of various types as are well known to the art, including both polar and non-polar solvents, but the polar solvents are particularly preferred. Typical polar organic solvents include the carboxylic acids such as acetic acid ethers such as tetrahydrofuran and p-dioxane, alcohols such as t-butyl alcohol and methanol, ether alcohols such as polyglycols, nitriles such as acetonitrile, amides such as dimethyl formamide, ketones such as acetone, polar chlorinated hydrocarbons such as chloroform, as well as dimethyl sulfoxide, and the like. Non-polar solvents include the hydrocarbons and chlorinated hydrocarbons such as carbontetrachloride. It will be understood that a solvent is preferably chosen which is not susceptible to oxidation under the particular conditions selected for the oxidation.

While water can be used as the sole reaction medium, or an organic solvent can be used as the sole reaction medium, it is preferred to use a water-polar organic solvent mixture containing up to about 50 volume percent water, typically 5–10% water. When water is present, and acids are absent, the trivalent thallium produced will normally be converted into the hydroxide which will precipitate and can be readily recovered and converted into any desired thallic salt in conventional manner, e.g., the hydroxide can be converted to a thallic salt by reaction with the appropriate acid.

If, however, an anion corresponding to the anion of the thallous compound is present, then the thallic compound will be obtained in the form of a salt containing that anion. On the other hand, other thallic salts can be formed by supplying the appropriate anion, e.g., by adding nitric acid or a different carboxylic acid to the reaction mixture. For example, if the monovalent thallium is in the form of an acetate, then acetic acid is advantageously included in the reaction mixture so that all of the trivalent thallium will also be obtained in the form of the acetate. Sufficient acetic acid is of course present to provide the necessary molar molecular quantity. Similarly, if a benzoate is desired, then benzoic acid is added to the reaction medium. The thallium (III) compound can thus be obtained in various forms, as desired and, as mentioned, it can be in the same form as the thallium (I) compound supplied.

Thus, monovalent thallium compounds can be readily converted to trivalent thallium compounds, and the reaction medium containing the trivalent thallium compound produced can be used directly or after suitable treatment, such as filtration to remove the catalyst for epoxidation, or other reaction. The trivalent thallium compound can also be separated from the reaction medium by precipitation, evaporation of solvent, or the like, if desired.

The invention will be more fully understood by reference to the following examples of specific embodiments thereof but it will be understood that these examples are given for illustrative purposes only and are not intended as limitative of the invention. In the examples, determinations of the thallium (III) product were carried out by means of conventional complexiometric analyses using standard ethylene nitrilo tetraacetic acid. The reaction mixture is analyzed in each case at the end of the indicated reaction period.

EXAMPLE I

To a glass reaction vessel containing a 0.2 M solution of thallium (I) acetate in 90 volume percent tertiary butanol and 10 volume percent water, also containing acetic acid in 0.5 M concentration, along with 0.04 mol per liter of platinum supported on alumina in powdered form, the support containing 5% of the catalytic metal, is added tertiary butyl hydroperoxide (commercial 90% product) in an amount to provide a 0.2 M solution of TBHP. The vessel is sealed and agitated at 60° C. in a constant temperature bath for 4 hours. The reaction mixture is then filtered to remove catalyst and the filtered solids washed with 0.5 molar acetic acid. The combined filtrate is analyzed and the conversion to the thallium (III) compound is found to be 50%.

EXAMPLE II

Example I was repeated except that the reaction time was reduced to 1 hour. A 31% conversion is obtained.

EXAMPLE III

Example I was again repeated except that the reaction time is increased to 6 hours. A 57% conversion is obtained.

EXAMPLE IV

Example I was again repeated except that the reaction time is further increased to 17 hours. A 53% conversion is obtained.

EXAMPLE V

To a glass reaction vessel containing a 0.1 M solution of thallium (I) acetate in 0.5 M acetic acid (aqueous), along with 0.01 mol per liter of platinum supported on alumina in powdered form, the support containing 5% of the catalytic metal, is added 90% tertiary butyl hydroperoxide in an amount to provide a 0.4 M solution. The vessel is sealed and agitated at 20° C. in a constant temperature bath for 19 hours. The reaction mixture is then filtered to remove catalyst and the filtered solids washed with 0.5 molar acetic acid. The combined filtrate is analyzed and the conversion to the thallium (III) compound is found to be 36%.

EXAMPLE VI

To a glass reaction vessel containing a 0.1 M solution of thallium (I) acetate in 0.5 M acetic acid (aqueous), along with 0.01 mol per liter of platinum supported on alumina in powdered form, the support containing 5% of the catalytic metal, is added 90% tertiary butyl hydroperoxide in an amount to provide a 0.1 M solution. The vessel is sealed and agitated at 20° C. in a constant temperature bath for 19 hours. The reaction mixture is then filtered to remove catalyst and the filtered solids washed with 0.5 molar acetic acid. The combined filtrate is analyzed and the conversion to the thallium (III) compound is found to be 49%.

EXAMPLE VII

Example VI is repeated except that the amount of catalyst is increased to 0.02 mol per liter. A conversion of 58% is obtained.

EXAMPLE VII

Example VI is again repeated except that the amount of catalyst is increased to 0.033 per liter. A conversion of 62% is obtained.

EXAMPLE IX

To a glass reaction vessel containing a 0.1 M solution of thallium (I) acetate in 0.5 M acetic acid (aqueous), along with 0.04 mol per liter of platinum oxide ($PtO_2$) in finely divided form, was added tertiary butyl hydroperoxide in an amount to provide a 0.4 M solution. The vessel was sealed and agitated at 60° C. in a constant temperature bath for 19 hours. The reaction mixture was then filtered to remove catalyst and the filtered solids washed with 0.5 molar acetic acid. The combined filtrate is analyzed and the conversion to the thallium (III) compound is found to be 46%.

EXAMPLE X

To a glass reaction vessel containing a 0.1 M solution of thallium (I) acetate in 0.5 M acetic acid (aqueous) along with 0.04 mol per liter of ruthenium supported on activated carbon in powdered form, the support containing 5% of the catalytic metal, is added tertiary butyl hydroperoxide in an amount to provide a 0.4 M solution. The vessel is sealed and agitated at 20° C. in a constant temperature bath for 19 hours. The reaction mixture is then filtered to remove catalyst and the filtered solids washed with 0.5 molar acetic acid. The combined filtrate is analyzed and the conversion to the thallium (III) compound is found to be 44%.

EXAMPLE XI

To a glass reaction vessel containing a 0.1 M solution of thallium (I) acetate in 0.5 M acetic acid (aqueous), along with 0.04 mol per liter of ruthenium oxide ($RuO_2$) in finely-divided form, is added tertiary butyl hydroperoxide in an amount to provide a 0.4 M solution. The vessel is sealed and agitated at 20° C. in a constant temperature bath for 19 hours. The reaction mixture is then filtered to remove catalyst and the filtered solids washed with 0.5 molar acetic acid. The combined filtrate is analyzed and the conversion to the thallium (III) compound is found to be 36%.

EXAMPLE XII

Example XI is repeated except that the amount of tertiary butyl hydroperoxide is reduced to a 0.1 M solution and the time is reduced to 4 hours. A conversion of 62% is obtained.

EXAMPLE XIII

To a glass reaction vessel containing a 0.05 M solution of thallium (I) benzoate in 50% tertiary butanol and 50 volume percent water, also containing benzoic acid in 0.25 M concentration, along with 0.04 mol per liter of platinum supported on alumina in powdered form, the support containing 5% of the catalytic metal, is added tertiary butyl hydroperoxide in an amount to provide a 0.2 M solution. The vessel is sealed and agitated at 20° C. in a constant temperature bath for 17 hours. The reaction mixture is then filtered and washed as in the preceding examples. A conversion of 16% is obtained.

EXAMPLE XIV

Example XIII is repeated except that the platinum catalyst is supported on activated carbon (5%). A conversion of 15% is obtained.

EXAMPLE XV

To a glass reaction vessel containing a 0.1 M solution of thallium (I) acetate in 50 volume percent tetrahydrofuran and 50 volume percent water, also containing acetic acid in 0.5 M concentration, along with 0.04 mol per liter of ruthenium supported on activated carbon in powdered form, the support containing 5% of the catalytic metal, is added tertiary butyl hydroperoxide in an amount to provide a 0.1 M solution. The vessel is sealed and agitated at 20° C. in a constant temperature bath for 17 hours. The reaction mixture is treated as in the previous examples and analysis of the combined filtrate shows a 10% conversion to the thallium (III) compound.

EXAMPLE XVI

To a glass reaction vessel containing a 0.1 M solution of thallium (I) acetate in 50 volume percent tertiary butanol and 50 volume percent water, also containing acetic acid in 0.5 M concentration, along with 0.04 mol per liter of ruthenium supported on activated carbon in powdered form, the support containing 5% of the catalytic metal, is added tertiary butyl hydroperoxide in an amount to provide a 0.4 M solution. The vessel is sealed and agitated at 20° C. in a constant temperature bath for 67 hours. The combined filtrate shows a 16.3% conversion to the thallium (III) compound.

EXAMPLE XVII

Example XV is repeated except that instead of ruthenium an equal molar quantity of platinum on alumina (5%) is used as catalyst. A 46.5% conversion is obtained.

EXAMPLE XVIII

Example XV is repeated except that instead of ruthenium on activated carbon an equal molar quantity of platinum on alumina is used as catalyst. A 46.5% conversion is obtained.

While the invention has been discussed above in specific connection with organic hydroperoxides of the formula ROOH, it will be understood that this formula also applies to peracids wherein R is an acyl or benzoyl group, e.g., peracetic acid, perbenzoic acid, and the like and the term "hydroperoxide" as used herein is thus intended to cover such peracids as well.

EXAMPLE XIX

Using the procedure of the previous examples, a solution of 0.2 M peracetic acid in 90 volume percent tertiary butanol and 10 volume percent water also containing 0.5 M benzoic acid and 0.2 M thallous benzoate along with 0.04 M platinum on alumina (5%) is stirred at room temperature for two hours. Conversion to the thallic compound is 45%.

What is claimed is:

1. A process for converting a thallium (I) compound to a thallium (III) compound which comprises reacting the thallium (I) compound with an organic hydroperoxide in a liquid medium in the presence of a Group VIII noble metal.

2. A process as defined in claim 1, wherein the Group VIII noble metal is platinum or ruthenium.

3. A process as defined in claim 1, wherein the hydroperoxide is t-butyl hydroperoxide.

4. A process as defined in claim 1, wherein the thallium (I) compound is a carboxylate.

5. A process as defined in claim 4, wherein the Group VIII noble metal is platinum or ruthenium.

6. A process as defined in claim 4, wherein the hydroperoxide is t-butyl hydroperoxide.

* * * * *